(12) United States Patent
Lang et al.

(10) Patent No.: US 7,345,173 B2
(45) Date of Patent: Mar. 18, 2008

(54) WORK-UP OF THE MOTHER LIQUOR OBTAINED IN THE PREPARATION OF HIGH-PURITY TRIETHYLENEDIAMINE

(75) Inventors: Ortmund Lang, Quirnbach (DE); Bernd Rumpf, Hockenheim (DE); Matthias Frauenkron, Ludwigshafen (DE); Dirk Funhoff, Mannheim (DE); Thomas Manderbach, Ludwigshafen (DE); Bernd Stein, Seeheim-Jugenheim (DE)

(73) Assignee: BASF SE, Ludwigshafen (DE)

( * ) Notice: Subject to any disclaimer, the term of this patent is extended or adjusted under 35 U.S.C. 154(b) by 1084 days.

(21) Appl. No.: 10/138,337

(22) Filed: May 6, 2002

(65) Prior Publication Data

US 2003/0004349 A1 Jan. 2, 2003

(30) Foreign Application Priority Data

May 10, 2001 (DE) ................................ 101 22 502

(51) Int. Cl.
*C07D 487/00* (2006.01)
(52) U.S. Cl. .................................................... 544/352
(58) Field of Classification Search ................. 544/352
See application file for complete search history.

(56) References Cited

U.S. PATENT DOCUMENTS

| 902,073 | A | 10/1908 | Gueritey | |
|---|---|---|---|---|
| 2,937,176 | A | 5/1960 | Herrick | 260/268 |
| 3,123,607 | A | 3/1964 | Farkas et al. | 260/268 |
| 3,297,701 | A | 1/1967 | Brader et al. | 260/268 |
| 3,993,651 | A | 11/1976 | Keating | 260/268 |
| 4,017,494 | A | 4/1977 | Bosche et al. | 260/268 |
| 4,182,864 | A | 1/1980 | Nieh et al. | 544/352 |
| 4,216,323 | A | 8/1980 | Otsuki et al. | 544/352 |
| 4,233,447 | A | 11/1980 | Nieh et al. | 544/352 |
| 4,289,881 | A | 9/1981 | Imre et al. | 544/352 |
| 4,757,143 | A | 7/1988 | Vanderpool et al. | 544/352 |
| 4,804,758 | A | 2/1989 | Hoelderich et al. | 544/352 |
| 5,741,906 | A | 4/1998 | Santiesteban et al. | 544/352 |
| 6,627,756 | B1 * | 9/2003 | Riechers et al. | 544/352 |

FOREIGN PATENT DOCUMENTS

| DE | 1 745 627 | 5/1970 |
|---|---|---|
| DE | 24 42 929 | 3/1976 |
| DE | 26 11 069 | 9/1976 |
| DE | 28 49 993 | 5/1979 |
| DE | 37 18 395 | 12/1987 |
| DE | 36 34 258 | 4/1988 |
| DE | 199 33 850 | 1/2001 |
| DE | 199 62 455 | 6/2001 |
| DE | 101 00 943 | 7/2002 |
| EP | 111 928 | 6/1984 |
| EP | 382 055 | 8/1990 |
| EP | 842 935 | 5/1998 |
| EP | 1070717 A1 * | 1/2001 |
| EP | 1 070 717 | 6/2001 |
| GB | 902073 | 7/1962 |
| GB | 2 080 283 | 2/1982 |
| GB | 2080283 | 2/1982 |
| JP | 49-048609 | 5/1974 |
| WO | WO 03/022851 | 3/2003 |

* cited by examiner

*Primary Examiner*—Mark L. Berch
(74) *Attorney, Agent, or Firm*—Novak Druce + Quigg LLP

(57) ABSTRACT

In a process for the purification of triethylenediamine (TEDA) in which TEDA is vaporized and the gaseous TEDA is passed into a liquid solvent and is subsequently crystallized from this, the mother liquor obtained after the TEDA has been crystallized is extracted with an extractant which is immiscible or only slightly miscible with the solvent of the mother liquor and in which TEDA is readily soluble, and the TEDA-depleted mother liquor obtained after extraction and/or the TEDA-enriched extractant which has been used for the extraction are/is returned to the process.

16 Claims, No Drawings

WORK-UP OF THE MOTHER LIQUOR OBTAINED IN THE PREPARATION OF HIGH-PURITY TRIETHYLENEDIAMINE

The present invention relates to a process for working-up mother liquor obtained in the preparation of triethylenediamine (TEDA) which has been subjected to a particular purification process. This purification process comprises vaporizing TEDA, passing it in gaseous form into a liquid solvent and crystallizing the TEDA from the resulting solution. The mother liquor obtained after this crystallization step is then worked-up according to the present invention.

TEDA is an important catalyst for the production of polyurethane foams. TEDA is solid at room temperature. Various methods are known for its preparation and purification, including the methods disclosed in the following publications:

DT-A 24 42 929; U.S. Pat. No. 3,297,701; DE-A 36 34 258; DE-A 17 45 627; DE-A 37 18 395; EP-A 111 928; EP-A 382 055; EP-A 842 935, EP-A 842 936; EP-A 831 096; EP-A 952 152 and U.S. Pat. No. 5,741,906.

The processes known hitherto for preparing TEDA lead to formation of product mixtures which comprise TEDA together with water, by-products such as piperazine and high molecular weight compounds and any solvent which may have been used in the reaction. TEDA is usually separated from these mixtures by batchwise or continuous distillation or rectification and is normally purified in a subsequent step by crystallization or recrystallization.

TEDA is comparatively difficult to handle without deterioration of the quality, in particular in respect of color and color stability, odor and purity, occurring.

The known, customary applications generally require a very pure, odorless and pure white TEDA. The following applications disclose processes which are said to give an appropriate TEDA quality:

DT-A 26 11 069; DE-A 28 49 993 and JP-A 49 048 609.

A disadvantage of these processes is that they do not give TEDA of the desired quality.

DE 19933850 and DE 19962455 by the Applicant relate to processes for preparing pure TEDA in which TEDA is vaporized and the gaseous TEDA is padded into a liquid solvent and the TEDA is crystallized from the solution.

DE 10100943 by the Applicant describes a process for preparing a solution of pure TEDA, which comprises vaporizing TEDA from a mixture comprising a solvent or a diluent which has a boiling point at atmospheric pressure in the range from 175 to 250° C. and passing the gaseous TEDA into a liquid solvent. Subsequent crystallization of the TEDA from the resulting solution gives pure TEDA of high quality.

After a solid/liquid separation of the crystalline TEDA from the solvent, a mother liquor comprising TEDA together with undesirable by-products and decomposition products is obtained in the last three processes. Owing to the impurities, the mother liquor cannot be reused in the process. Up to now, it has not been possible to work-up this mother liquor in such a way that it could be reused or the TEDA present in the mother liquor could be recovered at all. For this reason, the mother liquor was generally discarded. As a result, a large amount of solvent was necessary and the losses of TEDA remaining in the mother liquor were undesirably high.

It is an object of the present invention to provide a process for the recovery of TEDA which comprises vaporizing the TEDA used as starting material, passing the gaseous TEDA into a solvent and crystallizing the TEDA from the solution and which allows at least part of the solvents used to be recycled to the process and may also allow the yield of TEDA to be increased.

We have found that this object is achieved by a process for the purification of TEDA in which TEDA is vaporized and the gaseous TEDA is passed into a liquid solvent and is subsequently crystallized from this, wherein the mother liquor obtained after the TEDA has been crystallized is extracted with an extractant which is immiscible or only slightly miscible with the solvent of the mother liquor and in which TEDA is readily soluble, and the TEDA-depleted mother liquor obtained after extraction and/or the TEDA-enriched extractant which has been used for the extraction are/is returned to the process.

The first step of the process of the present invention comprises the reaction steps of the purification of TEDA as described in the applications DE 199 33 850.7, 199 62 455.0 and DE 101 00 943.7 by the Applicant. The processes for purifying TEDA described in these applications are an integral part of the process of the present application and are hereby incorporated by reference. The processes will be briefly described again below.

Passing the gaseous TEDA into a liquid solvent (TEDA quench) significantly reduces the formation of undesirable by-products which lead to a reduction in quality.

Many organic solvents are suitable for this TEDA quench. Examples include aliphatic, cyclic or acyclic hydrocarbons, in particular cyclic and acylic, branched or unbranched alkanes or alkane mixtures, for example n-pentane, i-pentane, cyclopentane, hexane, cyclohexane, heptane, octane and petroleum ether, chlorinated aliphatic hydrocarbons, in particular chlorinated alkanes, for example dichloromethane, trichloromethane, dichloro ethers and trichloro ethers, aromatic hydrocarbons, for example benzene, toluene and xylenes, chlorinated aromatic hydrocarbons, for example chlorobenzene, alcohols, for example methanol, ethanol, ethylene glycol, 1,4-butanediol and polyether alcohols, in particular polyalkylene glycols, for example diethylene glycol, dipropylene glycol, monethylene glycol and 1,4-butane diol, ketones, in particular aliphatic ketones, for example acetone, methyl ethyl ketone and diethyl ketone, aliphatic carboxylic esters, for example methyl acetate and ethyl acetate, aliphatic nitriles, for example acetonitrile and propionitrile, ethers, for example dioxane, THF, diethyl ether and ethylene glycol dimethyl ether and also mixtures of the solvents listed.

The solvent used for the TEDA quench is preferably an aliphatic hydrocarbon or a polyalkylene glycol, in particular a saturated cyclic or acyclic, aliphatic hydrocarbon having from 5 to 8 carbon atoms, for example pentane, hexane, cyclohexane or heptane, or dipropylene glycol. The crystallization of the pure TEDA from the TEDA solution prepared according to the present invention can be carried out by methods known to those skilled in the art. The TEDA crystals obtained by a subsequent, multistage or preferably single-stage crystallization are highly pure.

The gaseous TEDA is passed into the liquid solvent in a quenching apparatus, preferably a falling film condenser (thin film, trickle film or falling stream condenser) or in a nozzle apparatus. The gaseous TEDA can be conveyed in cocurrent or in countercurrent to the liquid solvent. It is advantageous to pass the gaseous TEDA into the quenching apparatus from above. Also advantageous is the tangential introduction of the liquid solvent at the top of the falling film condenser or introduction of the liquid solvent through one or more nozzles to achieve complete wetting of the inner wall of the quenching apparatus.

The amount of solvent used is chosen according to practical considerations. In general, the amount used is such that, depending on the type of solvent, solutions having a TEDA content of from about 1 to 50% by weight, preferably from 20 to 40% by weight, are obtained.

In general, the temperature in the TEDA quench is set to from 20 to 100° C., preferably from 30 to 60° C., by heating/cooling the solvent used and/or the quenching apparatus.

The absolute pressure in the TEDA quench is generally from 0.5 to 1.5 bar.

If, in the purification of the TEDA, the TEDA is, as described in DE 101 00 943.7, vaporized from a mixture with a solvent or diluent, preferably has a boiling point at atmospheric pressure of from 180 to 250° C., in particular from 180 to 230° C., especially from 190 to 210° C.

Particularly useful solvents or diluents which may be present in the mixture from which the TEDA is vaporized are inert polar aprotic solvents such as alkyl-2-pyrrolidones, for example N-methyl-2-pyrrolidone (NMP), 1-ethyl-2-pyrrolidone, 1,5-dimethyl-2-pyrrolidone, 1-isopropyl-2-pyrrolidone, ethers, for example diethylene glycol diethyl ether, triethylene glycol dimethyl ether and triethylene glycol diethyl ether, ketones, for example acetophenone and propiophenone, lactones, for example γ-buyrolactone, sulfoxides, for example dimethyl sulfoxide, carboxylic esters, for example dimethyl fumarate, nitriles, for example benzonitrile, and ureas, for example 1,3-dimethylimidazolidin-2-one (DMEU) and tetramethylurea, cyclic or acyclic hydrocarbons, in particular saturated cyclic or acyclic hydrocarbons, for example undecane, dodecane, cis-decalin and trans-decalin, chlorinated aliphatic hydrocarbons, for example 1-chlorooctane and 1,1-dichlorooctane, aromatic hydrocarbons, nitroaromatics and phenols, for example naphthalene, n-butylbenzene, phenol, cresol, nitrobenzene and nitrophenol, chlorinated aromatic hydrocarbons, for example 1,2-dichlorobenzene, benzyl chloride, 1,2,3,4-tetramethylbenzene and 1,2,3,5-tetramethylbenzene, alcohols, for example benzyl alcohol, 2-ethylhexanol, 1-octanol, i-decanol, 1,2-propanediol, 1,3-propanediol, ethylene glycol, diethylene glycol, 1,2-propylene glycol, 1,3-propylene glycol, 1,2-butanediol, 1,3-butanediol, 2,3-butanediol, 1,4-butanediol, neopentyl glycol, diethylene glycol monomethyl ether and dipropylene glycol, primary, secondary and tertiary amines, for example tri-n-butylamine, benzylamine, aniline, N-ethylaniline, N,N-dimethylaniline and N,N-diethylaniline, N-alkylamides, for example N-methylformamide and N-methylacetamide and mixtures thereof.

Particular preference is given to polar aprotic solvents or diluents having an $E^N_T$ of from 0.1 to 0.6, in particular from 0.2 to 0.5, especially from 0.3 to 0.45.

(For the definition of $E^N_T$, see Ch. Reichardt, Solvents and solvent effects in organic chemistry, 2nd Edition, VCH 1988).

Very particularly preferred solvents are NMP and ethylene glycol.

The solvent or diluent present in the mixture from which the TEDA is vaporized is preferably added to the crude or still contaminated TEDA after the synthesis of the TEDA.

The solvent or diluent can be used in a single pass or as a circulating solution after removal of the high boilers.

The amount of solvent or diluent used is chosen according to practical considerations. In general, the amount used is such that, depending on the type of solvent or diluent, solutions or mixtures having a TEDA content of from about 1 to 90% by weight, preferably from 40 to 70% by weight, are obtained.

The vaporization of the TEDA, optionally from a mixture of this with a solvent or diluent, can be carried out by methods and under conditions with which those skilled in the art are familiar, e.g. in a distillation or rectification apparatus in which the TEDA is placed, optionally together with the solvent or diluent.

The gaseous TEDA is preferably obtained at the top or at a side offtake of a distillation column. The gaseous TEDA in the process of the present invention generally has a purity of greater than 90% by weight, preferably greater than 95% by weight, in particular greater than 97% by weight.

If a mixture comprising TEDA and the solvent or diluent from which the TEDA is vaporized according to the present invention (e.g. the bottoms from the TEDA distillation column) is used, the temperature of the mixture is set to ≦230° C., preferably from 190 to 210° C., by selection of the solvent or diluent to be used, the TEDA content of the mixture and/or the pressure. The absolute pressure is generally from 0.1 to 5 bar, preferably from 0.5 to 1.5 bar.

The time between when the gaseous TEDA used in the process of the present invention is obtained and the TEDA quench is advantageously ≦10 seconds.

The TEDA to be purified can be obtained by known methods, e.g. by reaction of monoethanolamine, diethanolamine, triethanolamine, ethylenediamine, diethylenetriamine, triethylenetetramine, piperazine, N-(2-hydroxyethyl)piperazine, N,N'-bis(2-hydroxyethyl)piperazine, N-(2-aminoethyl)piperazine, N,N'-bis(2-aminoethyl)piperazine, morpholine, or mixtures thereof over a catalyst, for example metal pyrophosphates, metal phosphates, e.g. alkaline earth metal monohydrogen phosphate, zeolites, zirconium phosphates, $Al_2O_3$, $SiO_2$, phosphorus-containing $TiO_2$ or $ZrO_2$, at elevated temperature, generally from 250 to 450° C. The pressure is usually from 0.1 to 50 bar, in particular from 0.1 to 5 bar. The reaction can optionally be carried out in the presence of an inert polar aprotic solvent such as an N-alkylpyrrolidone, for example N-methylpyrrolidone, dioxane, THF, a dialkylformamide, for example dimethylformamide, a dialkylacetamide, for example dimethylacetamide, or an inert polar protic solvent, for example water, and an inert carrier gas, for example $N_2$ or Ar.

The TEDA is subsequently crystallized from the mother liquor and separated off by solid/liquid separation. The mother liquor obtained in this way is, according to the present invention, brought into intimate contact with an extractant in an extraction step. Mass transfer takes place in this step. The extractant is selected so that the TEDA is taken up by it. The by-products and decomposition products responsible for the reduction in the quality of the TEDA are likewise dissolved in the extractant. The mother liquor is thereby freed of these by-products and decomposition products and can be returned to the process.

After mass transfer is complete, the mother liquor which has been depleted in TEDA, by-products and decomposition products (raffinate phase) and the extractant which has been enriched in TEDA (extract phase) are separated.

The solvent used as extractant advantageously has the following properties:

The extractant should have a large miscibility gap with the solvent used in the crystallization step; the mutual solubility of extractant and solvent should be <10% by weight, preferably <1% by weight. TEDA should dissolve significantly better in the extractant than in the solvent which is used in the crystallization step. Furthermore, the extractant and the solvent used in the crystallization step should have a sufficient density difference. This aids separation of the extract phase and the raffinate phase. The density difference should preferably be >50 kg/m$^3$, in particular >100 kg/m$^3$.

Solvents which are preferred according to the present invention as extractants are water and water-miscible solvents such as lower alcohols or dihydric or polyhydric alcohols. Examples of suitable alcohols include methanol, ethanol, n-propanol, i-propanol, ethylene glycol, polyethylene glycol and glycerol. The alcohols can be used individually or as mixtures, optionally also in admixture with water. The most preferred extractant is water.

Since not only the TEDA but also the by-products and decomposition products formed in its synthesis and purification go into the extract phase during the extraction, this extraction gives a mother liquor (raffinate phase) which is free of TEDA and the undesirable by-products. The mother liquor can be recycled and reused as organic solvent into which gaseous TEDA is passed and from which it is subsequently crystallized. Such recycling is not possible in the case of a mother liquor which has not been worked up according to the present invention, since the impurities present in the mother liquor reduce the quality of the TEDA obtained.

The work-up according to the present invention of the mother liquor by means of an extractant can be carried out by the methods and under the conditions with which those skilled in the art are familiar, e.g. in an extraction apparatus into which the mother liquor is introduced continuously or batchwise, in each case together with the extractant.

The extraction according to the present invention reduces the amount of TEDA present in the mother liquor to values of <10% by weight, preferably <1% by weight, of the original value. The extract phase after the extraction according to the present invention accordingly contains >90% by weight, preferably >99% by weight, of the TEDA originally present in the mother liquor. Depending on the type of extractant used, solutions having a TEDA content of from about 1 to 40% by weight, preferably from 5 to 30% by weight, in particular 10-30% by weight, are obtained.

The extract phase, too, may if appropriate be recycled after the extraction according to the present invention has been carried out and be reused for the extraction. The degree of saturation of TEDA and by-products and intermediates in the extract phase will determine whether and how often the extract phase can be reused. Of course, the degree of saturation depends greatly on the nature of the solvent used as extractant and on the solubility of TEDA and the by-products and intermediates in this solvent. However, the extractant can also be taken from the process and worked up after a single extraction. This is done, in particular, when using water because of its ready availability.

When a certain degree of saturation has been reached, the solvent used for the extraction can no longer take up TEDA and by-product and can no longer be recirculated. This extract phase is then worked up and separated into the solvent used and TEDA, preferably by distillation. The solvent is then reused as extractant. Depending on the type and manner of work-up, TEDA of differing purity is obtained. In general, this is then returned to the purification process, i.e. vaporized, optionally from a mixture with a solvent or diluent, and condensed by passing it into an organic solvent and crystallized from this. The purification process described can also be carried out directly in the work-up of the extract phase by distillation of the TEDA leaving the column.

The process of the present invention allows the reuse of the solvent used in the crystallization of the TEDA and thus makes possible a reduction in the amount of fresh solvent required. The work-up of the extract phase and the recycling of the TEDA which is made possible in this way also increases the yield of TEDA compared to the way in which the process has been carried out hitherto.

In a preferred embodiment, the process of the present invention can be carried out as follows:

A TEDA-containing mixture which has been obtained, for example, as crude reaction product from a continuous process in which ethylenediamine and piperazine are reacted in a gas-phase reactor at from 320 to 420° C. and from 0.5 to 1.5 bar in the presence of a solvent (for example water), a carrier gas (e.g. $N_2$ or Ar) and a zeolite catalyst is fed into a distillation apparatus comprising a distillation column having about 15 theoretical plates. In this column, low boilers (for example ammonia, ethylamine, water) are separated off at a temperature at the top of from 95 to 120° C. and a pressure of generally from 500 mbar to 1.5 bar. The bottom product is pumped into a further distillation column having about 30 theoretical plates. At a temperature at the top of from 140 to 160° C. and a pressure of from 500 mbar to 1.5 bar, piperazine is separated off at the top of this column and is optionally fed back into the synthesis reactor.

The bottom product comprising TEDA and high boilers is pumped into a further distillation column having about 25 theoretical plates. At a pressure of from 500 mbar to 1.5 bar, the high boilers are discharged at the bottom of this column. At the top of the column, TEDA having a purity of >95% by weight, in particular >97% by weight, is taken off in vapor form via a partial condenser and is directly quenched in a solvent, preferably pentane and/or cyclohexane, at from 30 to 100° C., preferably from 30 to 60° C., in a falling film condenser and is dissolved at the same time (TEDA quench).

After the TEDA quench, TEDA is crystallized from the solution in a crystallization step by vaporization of the solvent at from 10 to 100° C., preferably from 20 to 40° C., and a pressure of from 0.1 to 5 bar, preferably from 0.5 to 1.5 bar, or by cooling to a temperature of generally from −10 to 40° C., preferably from 0 to 10° C.

The suspension taken off from the crystallizer is separated into high-purity TEDA and mother liquor in a solid/liquid separation, e.g. in a centrifuge. The mother liquor, which still contains residual TEDA, is then brought into intimate contact with an extractant, preferably water, at from 10 to 100° C., preferably from 20 to 40° C., and a pressure of from 0.1 to 5 bar, preferably from 0.5 to 1.5 bar, in an extraction step, for example in a mixer-settler or an extraction column.

The extract phase leaving the extraction after mass transfer and phase separation, which contains the major part of the TEDA and the undesirable by-products and decomposition products which lead to a reduction in the quality of the TEDA, is returned to the reactor or passed to a distillation. The TEDA obtained after distillation can be returned to the purification stage. The raffinate phase, which contains only traces of TEDA, is returned to the TEDA quench.

The invention is illustrated by the following examples.

EXAMPLES

Example 1

Comparative Example

The experiments were carried out in a 4 l (catalyst volume) salt bath reactor (shell-and-tube reactor containing 7 tubes, internal diameter 21 mm, length 2 m) made of stainless steel and heated by means of electric heating tapes. The pipes for the reactor feed, crude reaction product and the distillation section were partly configured as double-walled tubes and were oil-heated. The components of the plant were protectively heated and were individually matched to the temperature required in each case by use of different heating circuits. The catalyst used was a zeolite in the form of extrudates (diameter: about 2 mm, length: about 30 mm) (catalyst bed).

The feed of 1300 g/h together with 3 standard l/h (standard l=standard liters=volume at STP) of nitrogen were introduced at atmospheric pressure into the salt bath reactor heated to 350° C. (WHSV over the catalyst: 1 kg of feed per 1 of cat. (bed volume) and per h).

The feed had the following composition (figures in % by weight):

| | | |
|---|---|---|
| Ethylenediamine | 30% | |
| Piperazine | 20% | |
| Water | 50%. | |

The gaseous reaction product was condensed at 80° C. in a quench using circulated liquid which consisted of liquid reaction product which had been obtained previously (=reaction product quench).

Analysis of the condensate indicated the following composition (figures in % by weight):

| | |
|---|---|
| Ammonia | 3% |
| Piperazine | 17% |
| Triethylenediamine | 23% |
| Water | 54% |
| Remainder | high boilers and other by-products. |

The uncondensed material was, after a gas/liquid separator, conveyed to the distillation column.

Part of the liquid reaction product was cooled and used as circulated liquid (for the reaction product quench), while another part was pumped continuously to a distillation column by means of a pump. The glass column having a diameter of 50 mm was equipped with 30 bubble cap trays. The reflux ratio was about 1:1.

The low boilers (ammonia, ethylamine, water) were taken off in liquid form at the top of the column at atmospheric pressure and a temperature at the top of 96° C.

The bottom product from the distillation column was pumped continuously at 155° C. into a downstream distillation column.

The glass column having a diameter of 50 mm was equipped with 60 bubble cap trays. The reflux ratio was about 10:1. Piperazine was taken off in liquid form at the top of the column at atmospheric pressure and a temperature at the top of 150° C. and was recirculated to the reactor.

200 g/h of N-methyl-2-pyrrolidone were fed into the bottom of the column.

Analysis of the bottom product indicated the following composition (figures in % by weight):

| | |
|---|---|
| Piperazine | 0.03% |
| Triethylenediamine | 53% |
| N-methyl-2-pyrrolidone | 43% |
| Remainder | high boilers and other by-products. |

The bottom product from the distillation column was pumped continuously at 185° C. into the next distillation column. The glass column having a diameter of 50 mm was equipped with 50 bubble cap trays. The reflux ratio was about 8:1. The high boilers were discharged continuously at 200° C. from the bottom of the column, and the temperature of the oil-heated vaporizer was 230° C. At the top of the column, TEDA was taken off in vapor form and quenched at about 30° C. in pentane as solvent (mixture of 80% by weight of n-pentane and 20% by weight of isopentane) and simultaneously dissolved (=TEDA quench). For the TEDA quench, use was made of a falling film condenser (trickle film condenser or falling stream condenser) into which gaseous TEDA was introduced from the top. Pentane was fed in tangentially at the top of the falling film condenser. The resulting solution had the following composition (figures in % by weight):

| | |
|---|---|
| Pentane | 94% |
| Piperazine | 0.01% |
| Triethylenediamine | 5% |
| Remainder | by-products. |

After the partial removal of pentane by evaporative crystallization at 25° C. and a pressure of 570 mbar, crystalline TEDA was separated from the mother liquor on a suction filter. TEDA was obtained in a purity of at least 99.5% by weight.

Part of the mother liquor was recirculated together with the pentane obtained in the evaporative crystallization and 200 g/h of fresh pentane back to the TEDA quench. To prevent accumulation of undesirable by-products and decomposition products which lead to a reduction in the quality of the TEDA, about 200 g/h of mother liquor were bled off from the circuit.

Analysis of the mother liquor bled off indicated the following composition (figures in % by weight):

| | |
|---|---|
| Pentane | 95% |
| Piperazine | 0.02% |
| Triethylenediamine | 4.7% |
| Remainder | by-products. |

Example 2

According to the Present Invention

The experiment was carried out as described in example 1, but the mother liquor was mixed with water in a ratio of about 1:1, shaken and, after separation of the phases, analyzed.

Analysis of the extract phase indicated the following composition (figures in % by weight):

| | |
|---|---|
| Pentane | <0.01% |
| Piperazine | 0.02% |
| Triethylenediamine | 4.4% |
| Water | 95.5% |
| Remainder | by-products. |

Analysis of the raffinate phase indicated the following composition (figures in % by weight):

| | |
|---|---|
| Pentane | 99.95% |
| Piperazine | <0.001% |
| Triethylenediamine | 0.02% |
| Water | 0.02% |
| Remainder | by-products. |

The extract phase can be returned to the reactor and the raffinate phase can be recirculated together with the pentane obtained in the evaporative crystallization and 50 g/h of fresh pentane back to the TEDA quench.

The recirculation enables the amount of fresh pentane to be reduced by about 75% and likewise enables the TEDA loss resulting from the bleeding-off of mother liquor to be reduced by about 75%.

Example 3

According to the Present Invention

The experiment was carried out as described in example 1, but the mother liquor was mixed with water in a ratio of about 1:4, shaken and, after separation of the phases, analyzed.

Analysis of the extract phase indicated the following composition (figures in % by weight):

| | |
|---|---|
| Pentane | <0.01% |
| Piperazine | 0.2% |
| Triethylenediamine | 23.6% |
| Water | 71.7% |
| Remainder | by-products. |

Analysis of the raffinate phase indicated the following composition (figures in % by weight):

| | |
|---|---|
| Pentane | 99.92% |
| Piperazine | >0.001% |
| Triethylenediamine | 0.04% |
| Water | 0.01% |
| Remainder | by-products. |

The extract phase can be returned to the reactor and the raffinate phase can be recirculated together with the pentane obtained in the evaporative crystallization and 50 g/h of fresh pentane back to the TEDA quench.

The recirculation enables the amount of fresh pentane to be reduced by about 75% and likewise enables the TEDA loss resulting from the bleeding-off of mother liquor to be reduced by about 75%.

We claim:

1. A process for the purification of triethylene-diamine (TEDA) in which TEDA is vaporized and the gaseous TEDA is passed into a liquid solvent and is subsequently crystallized from this, wherein the mother liquor obtained after the TEDA has been crystallized is extracted with an extractant which is immiscible or only slightly miscible with the solvent of the mother liquor and in which TEDA is readily soluble, and the TEDA-depleted mother liquor obtained after extraction is returned to the process and reused as organic solvent into which gaseous TEDA is passed, and/or the TEDA-enriched extractant which has been used for the extraction is returned to the process, and reused for extraction.

2. A process as claimed in claim 1, wherein the TEDA is vaporized from a mixture comprising a diluent or solvent which has a boiling point at atmospheric pressure of from 175 to 250° C. before being passed into the liquid solvent.

3. A process as claimed in claim 1, wherein the extractant is <10% soluble in the solvent and the solvent is <10% soluble in the extractant.

4. A process as claimed in claim 3, wherein the mutual solubility is <1% by weight.

5. A process as claimed in claim 1, wherein the desity difference between the extractant and the solvent used in the crystalization step is >50 kg/m$^3$.

6. A process as claimed in claim 5, wherein the density difference is >100 kg/in$^3$.

7. A process as claimed in claim 1, wherein the extractant is selected from the group consisting of water, lower alcohols and dihydric and polyhydric alcohols.

8. The process as claimed in claim 7, wherein the extractant is selected from the group consisting of water, methanol, ethanol, n-propanol, i-propanol, ethylene glycol, polyethylene glycol, glycerol and mixtures thereof.

9. A process as claimed in claim 8, wherein the extractant is water.

10. The process as claimed in claim 1, wherein the solvent used in the crystallization step is selected from the group consisting of cyclic and acyclic hydrocarbons, chlorinated aliphatic hydrocarbons, aromatic hydrocarbons, alcohols, ketones, aliphatic carboxylic acids, aliphatic nitriles and esters.

11. A process as claimed in claim 10, wherein the solvent is pentane and/or dipropylene glycol.

12. A process as claimed in claim 1, wherein the extraction is carried out so that the amount of TEDA present in the mother liquor is reduced to <10% by weight.

13. The process as claimed in claim 12, wherein the amount of mother liquor is reduced to <1% by weight.

14. The process as claimed in claim 1, wherein the extraction of the mother liquor is carried out continuously.

15. The process as claimed in claim 1, wherein the extraction of the mother liquor is carried out batchwise.

16. The process as claimed in claim 14, wherein the extraction is carried out in an extraction apparatus.

* * * * *